(12) United States Patent
Nagai et al.

(10) Patent No.: US 8,597,935 B2
(45) Date of Patent: Dec. 3, 2013

(54) CLASSIFICATION OF BLOOD CELLS AND APPARATUS THEREFORE

(75) Inventors: Yutaka Nagai, Tokyo (JP); Shigeko Yamamoto, Tokyo (JP)

(73) Assignee: Nihon Kohden Corporation, Tokyo (JP)

(*) Notice: Subject to any disclaimer, the term of this patent is extended or adjusted under 35 U.S.C. 154(b) by 678 days.

(21) Appl. No.: 12/297,517

(22) PCT Filed: Jan. 29, 2007

(86) PCT No.: PCT/JP2007/051353
§ 371 (c)(1),
(2), (4) Date: Oct. 17, 2008

(87) PCT Pub. No.: WO2007/129485
PCT Pub. Date: Nov. 15, 2007

(65) Prior Publication Data
US 2009/0130647 A1     May 21, 2009

(30) Foreign Application Priority Data

Apr. 21, 2006   (JP) ................. 2006-117883

(51) Int. Cl.
*C07K 1/00*     (2006.01)
(52) U.S. Cl.
USPC ........................................ 435/269; 435/372
(58) Field of Classification Search
USPC ................................................ 435/269, 372
See application file for complete search history.

(56) References Cited

U.S. PATENT DOCUMENTS

| | | | | |
|---|---|---|---|---|
| 3,883,247 | A * | 5/1975 | Adams | 356/39 |
| 4,325,706 | A * | 4/1982 | Gershman et al. | 435/6 |
| 5,540,494 | A | 7/1996 | Purvis, Jr. et al. | |
| 6,133,995 | A | 10/2000 | Kubota | |
| 2001/0053551 | A1 | 12/2001 | Jiang et al. | |

FOREIGN PATENT DOCUMENTS

| | | |
|---|---|---|
| JP | 4-326061 | 11/1992 |
| JP | 5-322882 | 12/1993 |
| JP | 2002-5925 | 1/2002 |

OTHER PUBLICATIONS

Zheng et al. "A micro device for separation of erythrocytes and leukocytes in human blood", Proceedings of the 2005 IEEE, 2005, p. 1024-1027.*
Alam et al. "Cell cycle kinetics of expanding populations of neural stem and progenitor cells in vitro", Biotechnology and Bioengineering, 2004, 88(3):332-347.*
Saito-Ito et al. "A rapid, simple and sensitive flow cytometric system for detection of *Plasmodium falciparum*", Parasitology International, 2001, 50:249-257.*
Thaer et al. "Microscope fluorometric investigations on the reticulocytic maturation distribution as diagnostic criterion of disordered erythropoiesis", Blut, Band 30, Seite 339-348, 1975.*
Supplementary European Search Report issued by the European Patent Office for European Application No. EP 07 70 7584, 2009.
Schmitz et al., "Optimization of Flow-Cytometric Discrimination Between Reticulocytes and Erythrocytes," Cytometry (1986), 7:439-444.
International Search Report issued by the Japanese Patent Office for International Application No. PCT/JP2007/051353 dated May 15, 2007.
European Examination Report issued by the European Patent Office for European Application No. EP 07 70 7584 on Mar. 31, 2011.
Jain et al, "Use of flow cytometry for determination of differential leukocyte counts in bovine blood," Am J. Vet. Res. (Apr. 1991) 52(4):630-36.
Y. Nagai et al., "Determination of red cells, nucleic acid-containing cells and platelets (RNP Determination) by a crossover analysis of emission DNA/RNA light," *Int. J. Lab. Hematol.* 31: 420-429 (2009).

* cited by examiner

*Primary Examiner* — Bin Shen
(74) *Attorney, Agent, or Firm* — Finnegan, Henderson, Farabow, Garrett & Dunner, L.L.P.

(57) ABSTRACT

A method and an apparatus using acridine orange for sorting particles to precisely carry out the measurement of cells in the blood are provided. The cells in the blood is sorted by the steps of staining cells in the blood with acridine orange, irradiating light on the cells in the blood, determining staining behavior using platelets as a staining indicator, and sorting the cells in the blood.

9 Claims, 5 Drawing Sheets

CLASSIFICATION OF BLOOD CELLS AND APPARATUS THEREFORE

TECHNICAL FIELD OF THE INVENTION

The present invention relates to the sorting of cells in the blood. In particular, the present invention relates to a method and apparatus for sorting particles, where measurement is carried out on reticulocytes, red blood cells and platelets.

BACKGROUND ART

It has been proposed to carry out both leukocytes classification and reticulocytes measurement by staining with acridine orange, fluorescent dye, in a single apparatus (see Patent Document 1).

Furthermore, it has been proposed to carry out leukocytes classification, reticulocytes measurement and blood-cell counting by staining with acridine orange, fluorescent dye, in a single apparatus (see Patent Document 2).

Patent Document 1: Japanese Patent Laying-Open No. 4-326061

Patent Document 2: Japanese Patent Laying-Open No. 5-322882

DISCLOSURE OF THE INVENTION

Problems to be Solved by the Invention

Conventionally, however, the quality of staining with acridine orange has not been considered in the art. Thus, problems of incorrect measurement of cells, such as reticulocytes count, with excess or insufficient stain have been caused.

In addition, a conventional blood analyzer using a flow cytometer, there is a problem in that the preparation of a sample with a staining agent may require a staining time of 30 minutes or more.

Furthermore, an increase in background level of a measurement apparatus has sometimes occurred due to the presence of noncellularly derived particles such as dusts in a cell suspension.

Therefore, an object of the present invention is to carry out accurate measurement of red blood cells and/or platelets by using acridine orange and platelets as a staining indicator.

In addition, another object of the present invention is to accurately measure the number of red blood cells and the number of platelets by sorting cells and noncellularly derived particles in the blood on the basis of values obtained by normalizing fluorescence intensities of cells obtained by staining the cells with acridine orange with respect to the sizes and shapes of the cells.

Means of Solving the Problems

A particle-sorting method using acridine orange to sort cells in blood as described in claim 1 of the present invention includes the steps of: staining cells in the blood with acridine orange; irradiating light on the cells in the blood; determining staining behavior using platelets as a staining indicator; and sorting the cells in the blood.

A particle-sorting method using acridine orange to sort cells in blood as described in claim 2 of the present invention includes the steps of: staining cells in the blood with acridine orange; irradiating light on the cells in the blood; normalizing the fluorescence intensities of the cells on the basis of the sizes and shapes of the cells; and sorting the cells in the blood on the basis of values obtained by the normalization.

A particle-sorting method using acridine orange to sort cells in blood as described in claim 3 of the present invention includes the steps of: staining cells in the blood with acridine orange; irradiating light on the cells in the blood; normalizing the fluorescence intensities of the cells on the basis of the sizes and shapes of the cells; determining staining behavior using platelets as a staining indicator; and sorting the cells in the blood on the basis of values obtained by the normalization.

In the particle-sorting method using acridine orange to sort cells in the blood as described in claim 3 of the present invention, the step of determining the staining behavior using platelets as a staining indicator may include making a decision from an orange-fluorescence component and/or green-fluorescence component of the platelets. In other words, a part colored with fluorescent green color (i.e., a green-fluorescence component) and a part colored with fluorescent orange color (i.e., an orange-fluorescence component) on the basis of detected electric signals are respectively normalized with the sizes (FS) or shapes (SS) of the cells, the center values of the respective distributions of red blood cells and platelets are measured from the normalized data, and the distance between them is then calculated to determine the staining behavior. By the way, in the fluorescent staining with acridine orange, the dye is intercalated between base pairs in a double-stranded DNA to generate fluorescence (green) mainly at a wavelength of 530 nm, while the dye causes stacking on a single-stranded nucleic acid such as RNA by electrostatic interaction to generate fluorescence (orange) mainly at a wavelength of 640 nm. Thus, both the orange-fluorescence component and the green-fluorescence component can be used as standards for the determination.

As described in claim 5 of the present invention, the particle-sorting method using acridine orange to sort cells in blood further includes the steps of: detecting scattered light and fluorescence generated by irradiating light on the cells in the blood as electric signals; making a RNA histogram of red blood cells on the basis of the detected electric signals; and detecting a right-side address of the half peak of the RNA while detecting an doubled address thereof to sort a cluster on the right side as reticulocytes.

As described in claim 6 of the present invention, the particle-sorting method using acridine orange to sort cells in the blood, further includes the steps of: detecting forward-scattered light and fluorescence generated by irradiation of light on cells in blood; and sorting cells, cellularly derived particles such as cell fragments, and noncellularly derived particles such as dusts using a scattergram in which the intensity of green fluorescence and the intensity of orange fluorescence of the cells are normalized with the sizes and shapes of the cells.

In the particle-sorting method using acridine orange to sort cells in the blood as described in claim 7 of the present invention, the light irradiated on the cells in the blood may have a center wavelength of 408 nm, 445 nm, 473 nm, or 488 nm.

In the particle-sorting method using acridine orange to sort cells in the blood as described in claim 8 of the present invention, the step of staining cells in the blood with acridine orange may include setting a sample prepared by mixing a staining agent containing acridine orange and a buffer with a blood specimen to a predetermined temperature, followed by staining the sample for a predetermined time.

In the particle-sorting method using acridine orange to sort cells in the blood as described in claim 9 of the present invention, the cells to be sorted may include red blood cells, platelets, red blood cell fragments, nucleated red blood cells, malaria parasites, and Howell-Jolly bodies.

A particle sorter as described in claim 10 includes: a light source for irradiating light on cells in blood; a flow cell for flowing a sample; a forward-scattered light detector for detecting forward-scattered light; a lateral-scattered light detector for detecting lateral-scattered light; a fluorescence detector for detecting fluoresce; means for determination of staining, by which the quality of staining platelets is determined; and means for determining reticulocytes or platelets.

A particle sorter as described in claim 11 of the present invention includes: a light source for irradiating light on the cells in the blood; a flow cell for flowing a sample; a forward-scattered light detector for detecting forward-scattered light; a lateral-scattered light detector for detecting lateral-scattered light; a fluorescence detector for detecting fluorescence; means for normalization, by which the fluorescence intensities of the cells on the basis of the sizes and shapes of the cells are normalized on the basis of the sizes and shapes of the cells; and means for sorting cells and noncellularly derived particles in the blood on the basis of values obtained by the normalization.

A particle sorter as described in claim 12 of the present invention includes: a light source for irradiating light on cells in blood; a flow cell for flowing a sample; a forward-scattered light detector for detecting forward-scattered light; a lateral-scattered light detector for detecting lateral-scattered light; a fluorescence detector for detecting fluorescence; means for normalization, by which the fluorescence intensities of the cells on the basis of the sizes and shapes of the cells are normalized on the basis of the sizes and shapes of the cells; means for determination of staining, by which the quality of staining platelets is determined; means for determination of staining, by which the quality of staining platelets is determined; and means for sorting cells and noncellularly derived particles in the blood on the basis of a normalized value.

Effects of the Invention

The particle-sorting method as described in claim 1 of the present invention carries out measurement of well-stained cells. Thus, the method can accurately sort cells in the blood, particularly reticulocytes, red blood cells and platelets, and subject them to measurement.

The particle-sorting method as described in any of claims 2 and 3 of the present invention carries out measurement of cells in the blood on the basis of a normalized value. Thus, the method can accurately sort cells and subject them to measurement.

The particle-sorting method as described in claim 4 of the present invention carries out measurement of well-stained cells using platelets as a staining indicator. Thus, the method can accurately sort cells in the blood, particularly reticulocytes and platelets, and subject them to measurement.

The particle-sorting method as described in claim 6 of the present invention can sort cells and noncellularly derived particles in the blood and then precisely sort and count red blood cells and platelets.

The particle-sorting method as described in claim 7 of the present invention can favorably detect a S/N level without an influence of autologous fluorescence from red blood cells as the light illuminated on cells in the blood has a center wavelength of 408 nm, 445 nm, 473 nm or 488 nm.

The particle-sorting method as described in claim 8 of the present invention can quickly carry out staining by holding a sample prepared by mixing a staining agent containing acridine orange and a buffer with a blood specimen at a predetermined temperature and subjecting the sample to the staining for a predetermined time.

The particle-sorting method as described in claim 9 of the present invention can accurately sort red blood cells, platelets, red blood cell fragments, nucleated red blood cells, malaria parasites and Howell-Jolly bodies.

The particle sorter as described in claim 10 of the present invention measures well-stained cells, so that it can accurately sort and measure cells in the blood, particularly reticulocytes and platelets.

The particle sorter as described in any of claim 11 and claim 12 of the present invention can accurately count red blood cells and platelets by sorting cells and noncellularly derived particles in the blood on the basis of values obtained by the normalization of fluorescence intensities of cells with the sizes and shapes thereof.

BEST MODE FOR CARRYING OUT THE INVENTION

Hereinafter, a method and apparatus for sorting cells in the blood will be described in detail as embodiments of the particle-sorting method and apparatus of the present invention with reference to the drawings.

Figure 1:
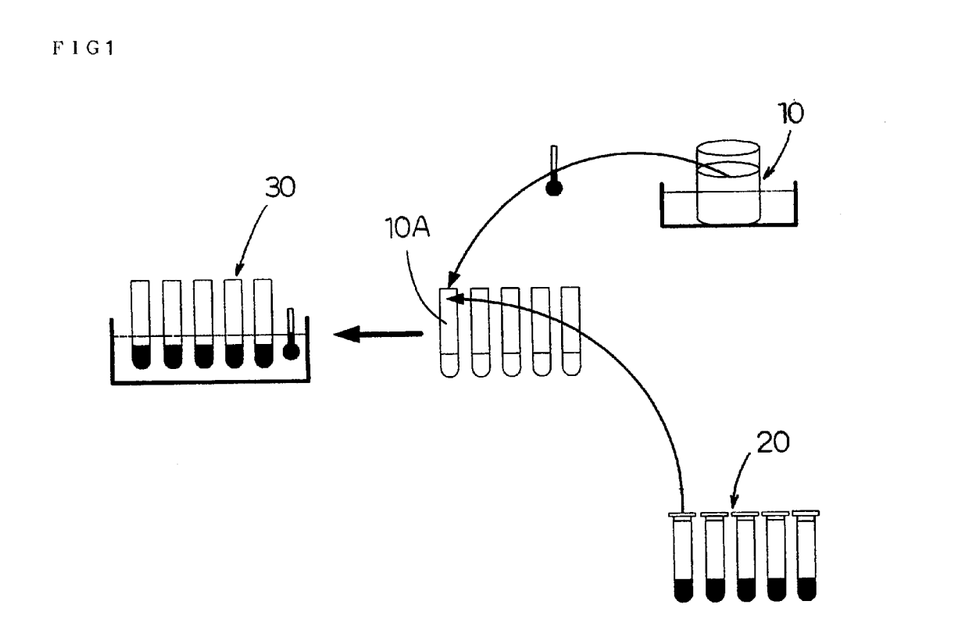
FIG. 1 is a schematic diagram illustrating the preparation of a measurement sample.

FIG. 1 is a schematic diagram illustrating the preparation of a measurement sample. At first, a particle-sorting method in accordance with the present invention includes: preparing a sample by mixing a sample of blood components containing cells in the blood with a staining agent to react them with each other; irradiating light on the sample at a detection area to detect scattered light and fluorescence generated from the cells in the sample as electric signals; and analyzing the cells in the blood components on the basis of the detected electric signals.

[Preparation of a Measurement Sample]

In the present invention, as a sample for carrying out measurement, the preparation of a sample of collected blood components is carried out. In this case, as illustrated in FIG. 1, a staining agent 10 is heated at a temperature of 20 to 50° C. when a required amount of the staining agent 10A is divided into predetermined-volume fractions. A predetermined amount of a sample 20 containing blood components is added to the divided staining agent 10A being heated and then stirred for 5 to 10 seconds. An obtained sample 30 is kept warm at 20 to 50° C. for 10 to 40 seconds. Consequently, according to the present invention, the preparation of the sample 30 can be completed within 15 to 60 seconds.

Therefore, in the present embodiment, 1-ml aliquots from the staining agent are dispensed into the respective tubes and the dispensed staining agent 10A in each tube is then added with 2·l of the sample 20 which is prepared so that the cell count for the measurement can be approximately $1 \times 10^7$ cells/··l. The staining agent 10 to be used is acridine orange in an amount of 0.5 to 1.5 mg/dl as a dye concentration adjusted by a Tris buffer at pH 7.4. In particular, a preferable dye concentration is 0.75 mg/dl. An appropriate sample 30 can be prepared by dividing the dye agent 10 into 1-ml dye agent fractions while heating at 45° C., adding 2 ml of the sample 20 to the heated 1-ml dye agent 10A followed by stirring for 5 seconds, and holding an obtained sample at 45° C. for 30 seconds. Alternatively, it may be prepared by successively adding the sample 20 of the blood and a buffer (pH 6.4 to 8.2), such as a phosphate buffer or a Tris buffer, to acridine orange which is separately freeze-dried.

[Measurement and Analysis of Prepared Sample]

Figure 2:
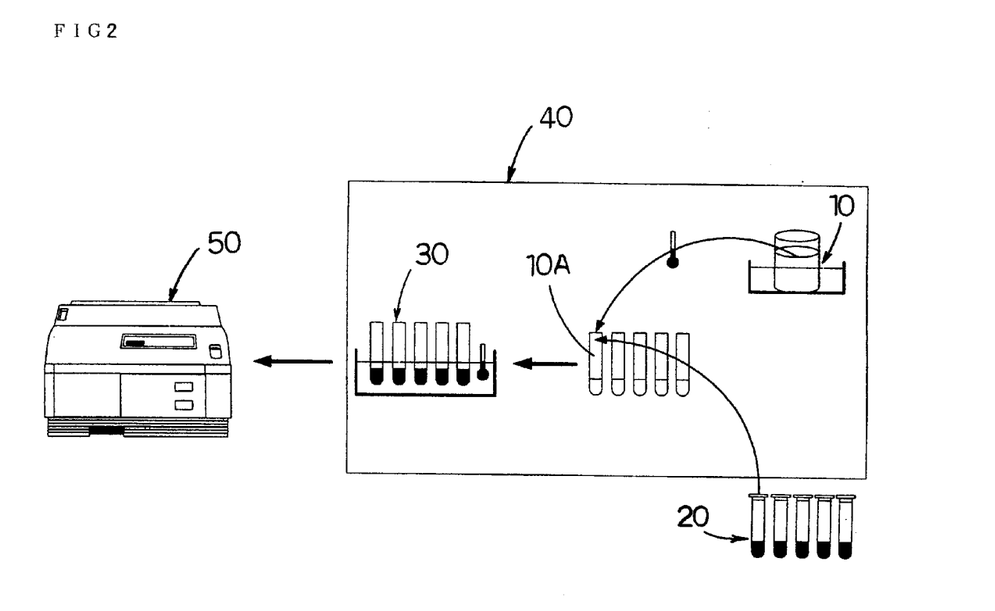
FIG. 2 is an explanation diagram illustrating a system as an apparatus for carrying out a method for sorting particles in accordance with the present invention.

FIG. 2 illustrates the configuration of a system as an apparatus for carrying out a method of sorting cells in blood components in accordance with the present invention. In FIG. 2, in other words, reference numeral 40 denotes the sample-preparing means for preparing a sample as described above. In addition, reference numeral 50 denotes a flow cytometer that includes a light-irradiating means for irradiating light on the sample 30 prepared by the sample-preparing means 40 in the detecting area, a cellular-parameter detecting means for detecting scattered light and fluorescence generated from cells in the irradiated sample, and a cell-analyzing means for analyzing cells in the blood components on the basis of the detected parameters of the cells. Furthermore, a processor 70 is provided for determining and normalizing staining behavior. By the way, in the case of the flow cytometer, the detecting area is provided as a flow cell.

Figure 3:
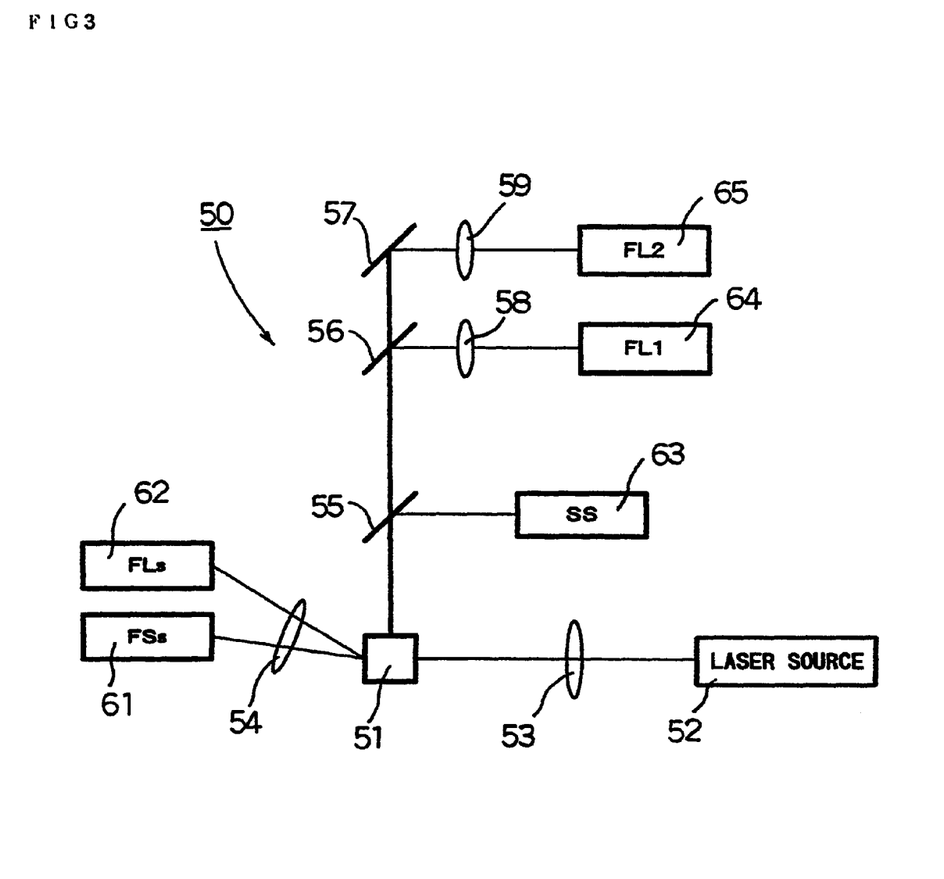
FIG. 3 is a systematic diagram illustrating the schematic configuration of a flow cytometer as an example of an apparatus for carrying out the method of sorting particles in accordance with the present invention.

FIG. 3 is a systematic diagram illustrating the schematic configuration of a flow cytometer as an embodiment of the apparatus for carrying out the method of sorting cells in blood components in accordance with the present invention. In FIG. 3, reference numeral 51 denotes a flow cell provided as a detecting area for the prepared sample. In addition, a laser source 52 is positioned in place with respect to the flow cell 51 through an irradiation-light condensing lens 53. The forward-scattered light obtained by irradiating light on the sample in the flow cell 51 is configured to be detected by each of a detector for small-angled forward-scattered light (FSs) 61 and a detector for large-angled forward-scattered light (FLs) 62 through a scattered-light condensing lens 54. Furthermore, the scattered light and fluorescence in the lateral direction obtained by irradiating the light on the sample in the flow cell 51 are detected by a lateral-scattered light detector (SS) 63 through a beam splitter 55, then detected by a first fluorescence detector (FL1) 64 through a beam splitter 56 and a wavelength-selective filter 58, and further detected by a second fluorescence detector (FL2) 65 through a beam splitter 57 and a wavelength-selective filter 59. Alternatively, dichroic mirrors may be used instead of the beam splitters.

Figure 4:
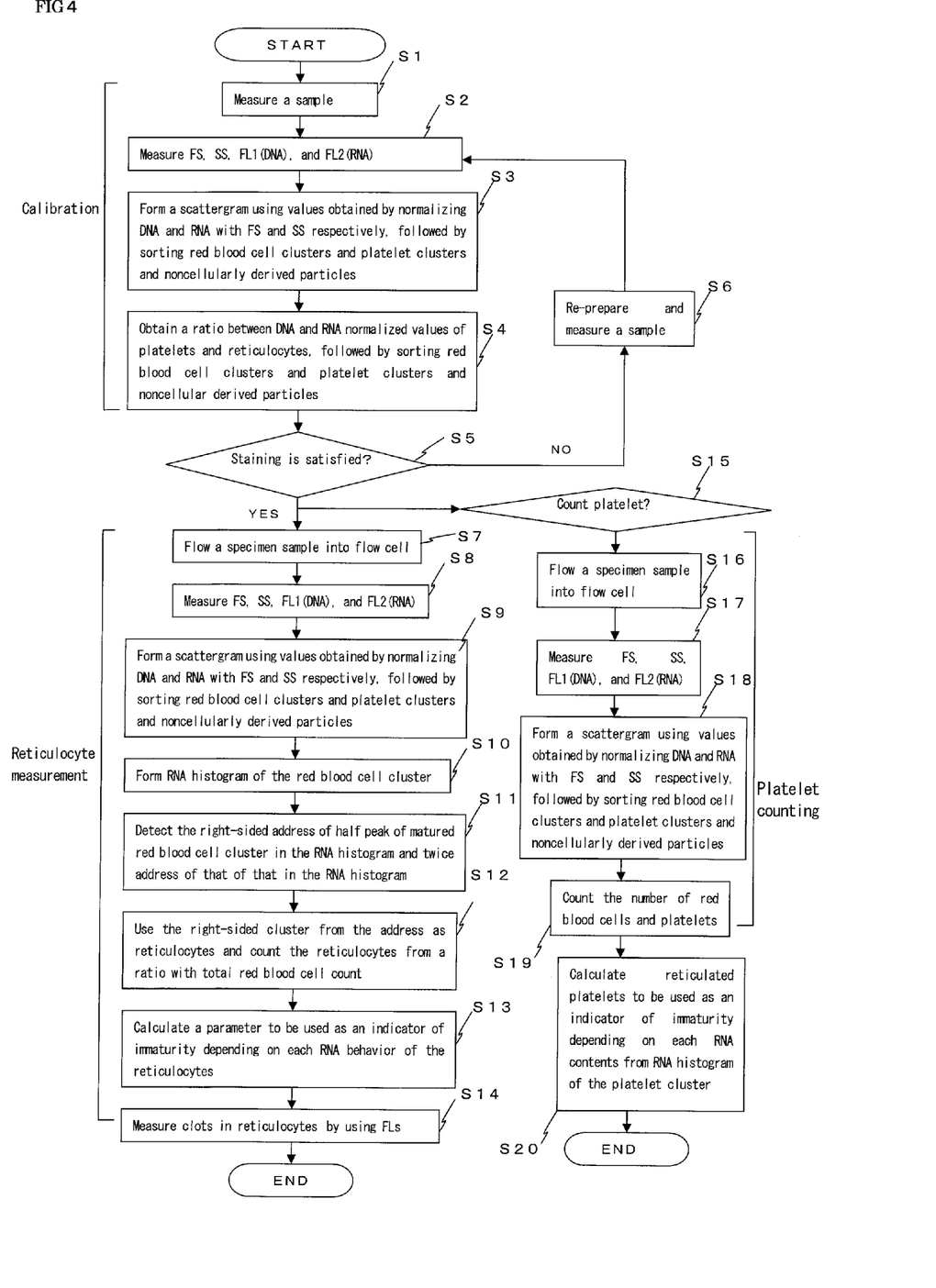
FIG. 4 is a flowchart illustrating a program for carrying out the method of analyzing cells in blood components using a flow cytometer that constitutes a the particle sorter shown in FIG. 3 in accordance with the present invention.

Then, a method for blood analysis in blood components in accordance with the present invention using the flow cytometer 50 as constructed above will be described with reference to the flowchart shown in FIG. 4.

At first, the sample of blood components prepared by the above sample-preparing means 40 is supplied to the flow cell 51 of the flow cytometer 50, followed by starting the calibration of the sample (STEP-1). Then, the sizes of red blood cells and platelets (FS), the amount of granules (SS), the amount of DNA (FL1) and the amount of RNA (FL2) are determined on the basis of electric signals detected by the detector for small-angled forward-scattered light (FSs) 61, the lateral-scattered light detector (SS) 63, the first fluorescence detector (FL1) 64 and the second fluorescence detector (FL2) 65, respectively (STEP-2). Then, the amount of DNA and the amount of RNA are normalized with FS and SS to form a scattergram. The scattergram when normalized with the size represents the scattergram of intracellular DNA concentration (cDNAc: cell DNA concentration) and intracellular RNA concentration (cRNAc: cell RNA concentration). A certain threshold level is defined on the scattergram to sort red blood cells and platelets (which are cells in the blood), cellularly derived particles and noncellularly derived particles (STEP-3).

Figure 6:
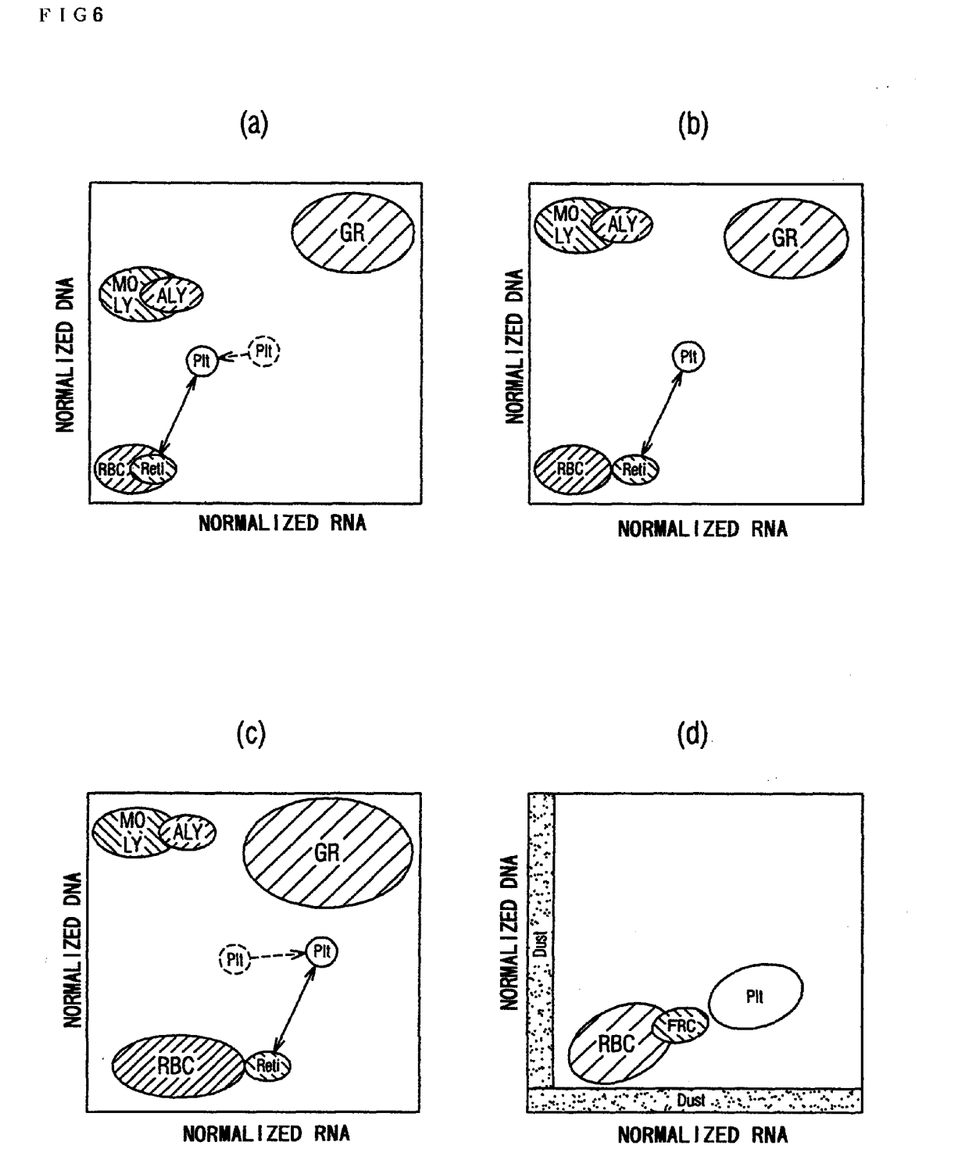
FIG. 6 is a diagram illustrating scattergrams (a), (b), and (c) of blood-component cells, each representing the state of platelet distribution as an indicator for the state of staining a sample prepared in the method of analyzing cells in blood components; and a scattergram (d) representing the sate in which cells and noncellularly derived particles are sorted in the method of analyzing cells in blood components as the particle-sorting method of the present Invention.

In this case, for example, if red blood cell-fragments, nucleated red blood cells, malaria parasites, and Howell-Jolly bodies are present in the sample, four distributions (red blood cells, red blood cell fragments, platelets and dusts) are present in the graph of (d) in FIG. 6. As shown in the graphs of (a) to (c) in FIG. 6, if the stained sample is of well-stained, the distribution of platelets and the distribution of red blood cells including reticulocytes are in a certain distance relationship in the scattergram of the normalized DNA/normalized RNA. In addition, if the staining is down well, the distribution position of platelets can be constant ((b) in FIG. 6). However, if the staining is poor and thin ((a) in FIG. 6) or dense ((c) in FIG. 6), a fluctuation in distribution position of platelets occurs. Thus, it is judged whether the sample is stained well or not by determining that the distribution position of the platelets is constant (STEP-4 and STEP-5).

In the normalized DNA/normalized RNA scattergram, the reticulocytes appear in the high-cRNAc region of the red blood cells distribution. Many of red blood cell fragments appear on a region between the red blood cells distribution and the platelets distribution. Nucleated red blood cells have their own nucleuses and more DNA components than others, so that they will appear on a region different from the red blood cells and the platelets in the normalized DNA/normalized RNA scattergram. Likewise, the Howell-Jolly bodies are nuclear fragments constructed of DNA, so that they will appear on a region different from the red blood cells and the platelets. Furthermore, all malaria parasites emit fluorescence, so that they will appear on a region different from the red blood cells and the platelets in the normalized DNA/normalized RNA scattergram.

When the staining is resulted in poor in the judgment of whether the sample is stained well or not, the sample is re-prepared and then subjected to the measurement procedures from STEP-1 as described above (STEP 5 and STEP 6). When the staining is resulted in good, the prepared sample is flown into the flow cell 51 of the flow cytometer 50 and the measurement of the sample is then started (STEP-7). In addition, criteria for the judgment of whether the sample is stained well or not will be described later.

Figure 5:
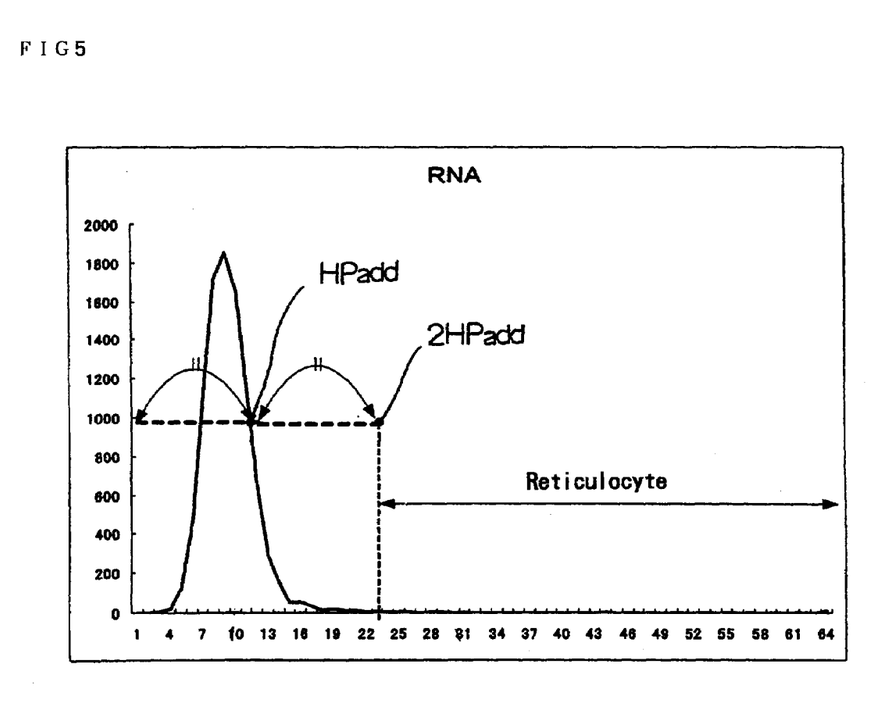
FIG. 5 is a RNA histogram illustrating the distribution of reticulocytes obtained from the cluster of red blood cells detected and measured by the method of analyzing cells in the blood components as the particle-sorting method of the present invention.

At first, the sizes of red blood cells and platelets (FS), the amount of granules (SS), the amount of DNA (FL1) and the amount of RNA (FLS) are determined on the basis of electric signals detected by the detector for small-angled forward-scattered light (FSs) 61, the lateral-scattered light detector (SS) 63, the first fluorescence detector (FL1) 64 and the second fluorescence detector (FL2) 65, respectively. The amount of DNA and the amount of RNA are normalized with their respective sizes, and a scattergram is formed. A certain threshold level is defined on the scattergram to sort red blood cells and platelets, and the numbers thereof are then counted, respectively (STEP-9). A RNA histogram of red blood cells is prepared (STEP-10). An example of the RNA histogram obtained in this case is illustrated in FIG. 5. An address HPadd of the right side of the half peak of a matured red blood cell cluster is detected in the RNA histogram and a doubled address thereof 2HPadd is then detected (STEP-11). Therefore, the cluster on the right side from the doubled-address 2HPadd can be calculated as the cluster of reticulocytes (STEP-12). Then, a parameter to be used as an indicator of immaturity can be calculated depending on the each RNA content of the reticulocytes (STEP-13). Furthermore, the clots in the reticulocytes can be measured on the basis of electric signals detected by the detector for large-angled forward-scattered light (FLs) 62 (STEP-14). Consequently, a series of measurement procedures is completed.

Next, the method of analyzing platelets in blood components in accordance with the present invention will be described with reference to the flowchart illustrated in FIG. 4. STEPS 1 to 6 for carrying out the judgment of whether the sample is stained well or not are the same as those described above. Thus, the explanations thereof are omitted in the following description. After carrying out the judgment of whether the sample is stained well or not (STEP-5), the setting for counting the platelets is carried out when the staining is resulted in good (STEP-15). Subsequently, the prepared sample is flown into the flow cell 51 of the flow cytometer 50 and the measurement of the sample is then started (STEP-16). At first, the sizes of red blood cells and platelets (FS), the amount of granules (SS), the amount of DNA (FL1) and the amount of RNA (FL2) are determined on the basis of electric signals detected by the detector for small-angled forward-scattered light (FSs) 61, the lateral-scattered light detector (SS) 63, the first fluorescence detector (FL1) 64 and the second fluorescence detector (FL2) 65 (STEP-17). Then, the amount of DNA and the amount of RNA are normalized with their respective FS and SS to form a scattergram. A certain threshold level is defined on the scattergram to sort the red blood cells, the platelets and other particles (STEP-18). Subsequently, a histogram is formed for the platelets, and the platelets are counted (STEP-19). Then, the number of reticulated platelets, which can be provided as an indicator of immaturity depending on the amount of RNA, is determined from the RNA histogram of the platelets (STEP-20). Consequently, the method can determine the number of platelets and the number of reticulated platelets, accurately.

In FIG. 6, (a), (b) and (c) represent scattergrams of cells in blood components, representing the states of platelet distributions for carrying out the above-described judgment of whether the sample is stained well or not, respectively. Each of the scattergrams is formed such that the vertical axis thereof represents the normalized DNA and the horizontal axis thereof represents the normalized RNA. The scattergrams represent the state in which the staining results in insufficient ((a) in FIG. 6), the state in which the staining results in good ((b) in FIG. 6), and the state in which the staining results in excess ((c) in FIG. 6), respectively. In the figure, by the way, "Reti" represents reticulocytes, "Plt" represents platelets, "RBC" represents red blood cells, "GR" represents granulated leukocytes, "MO" represents monocytes, "LY" represents lymphocytes, and "ALY" represents atypical lymphocytes.

Secondary granules, such as leukocytic eosinophils (EOS) and neutrophils (NEUT), can be stained vivid orange with acridine orange regardless of the staining quality. On the other hand, fluorescence components of reticulocytes which are stained orange with acridine orange (hereinafter, referred to as "orange-fluorescence components") and the orange-fluorescence components of platelets are less stained compared with reticulocytes. The staining intensities of these types of cells are proportional to each other. For example, in the case of insufficient staining, the orange fluorescence components of reticulocytes and platelets are not stained. In other words, the staining behaviors of reticulocytes and platelets can reflect the staining qualities thereof, respectively. Therefore, the determination of the quality of staining with acridine orange may use the staining behavior of platelets as an indicator as described below.

(1) [FIG. 6(a)] is the normalized DNA/normalized RNA scattergram in the state of insufficient staining. In this case, the RNA components of the reticulocytes are stained insufficiently, so that the reticulocytes have the same staining behavior as that of the matured red blood cells. As a result, the red blood cell distribution itself shifts down to the left. Simultaneously, the orange-fluorescence components of the platelets are also stained insufficiently, so that the platelets have the same staining behavior as that of the matured red blood cells. As a result, the platelet distribution itself also shifts down to the left. If the reticulocytes are counted without noticing the fact of insufficient staining, it results in spurious low counts of platelets.

(2) [FIG. 6(c)] is the normalized DNA/normalized RNA scattergram in the state of excess staining. This causes higher background and results in spurious excessive fluorescence of matured red blood cells, so that the matured red blood cells can be counted as reticulocytes. As a result, spurious high counts of the reticulocytes are obtained. In addition, the red blood cell distribution shifts up to the right. Simultaneously, for a similar reason, the platelet distribution also shifts up to the right.

(3) Therefore, the staining behavior of the platelets is used as an indicator. In the state of good staining (FIG. 6(b)), the distance between the platelet distribution and the red blood cell distribution is constant in the normalized DNA/normalized RNA scattergram. Thus, the distributed positions of platelets, red blood cells and reticulocytes are stable when the staining is carried out well. In addition, even if the staining is resulted in poor, the distribution distance is constant and variable in a similar manner. Therefore, the quality of staining reticulocytes can be confirmed by the location of distributed platelets and the distribution distance among platelets, red blood cells and reticulocytes.

The presence of noncellularly derived particles such as dusts in a cell suspension may lead to an increase in background of a measurement apparatus. In this case, a scattergram (the normalized DNA/normalized RNA scattergram), in which green fluorescence and orange fluorescence of cells are normalized with the sizes and shapes of the cells, is used. In other words, as shown in FIG. 6(d), utilizing the fact that noncellularly derived particles include extremely small green and orange fluorescence components compared with cells in the blood, it is found that cells such as red blood cells, reticulocytes, and platelets and cellularly derived particles including cell fragments such as red blood cell fragments (FRC) can be easily sorted from noncellularly derived particles such as dusts in the suspension.

While the preferred embodiment of the present invention has been described above, the invention is not limited thereto but various design changes and variations may be made without departing from the spirit of the invention. For instance, it will be obvious to those skilled in the art that the lateral dispersion include the information on the shape and amount of particles. In the present description, it is obvious that the description about the shape (SS) or the amount (SS) of the granules does not always intend to only represent the information on one of them.

EXPLANATION OF REFERENCE NUMERALS IN DRAWINGS 10 dye agent
10A dispensed dye agent
20 sample of blood components
30 prepared sample
40 sample-preparing means
50 flow cytometer
51 flow cell
52 laser source
53 condensing lens for condensing the irradiation light
54 condensing lens for condensing scattered light
55, 56, 47 beam splitter
58, 59 wavelength-selection filter
61 detector for small-angled forward-scattered light (FSs)
62 detector for large-angled forward-scattered light (FSs)
63 lateral-scattered light detector (SS)
64 fluorescence detector (FL1)
65 first fluorescence detector (FL2)
70 processor

The invention claimed is:

1. A particle-sorting method using acridine orange to sort cells in blood, comprising the steps of:
    staining cells in the blood with acridine orange;
    irradiating light on the cells in the blood;
    receiving the irradiated light with detectors;
    measuring the sizes of red blood cells and platelets by detecting forward scatter (FS) using a detector for small-angled forward-scattered light;
    measuring the amount of granules by detecting side scatter (SS) using a detector for lateral-scattered light;
    measuring the amount of DNA by detecting a first fluorescence (FL1) using a first fluorescence detector;
    measuring the amount of RNA by detecting a second fluorescence (FL2) using a second fluorescence detector;
    determining the intracellular DNA concentration and intracellular RNA concentration by dividing
    the amount of DNA (FL1) and the amount of RNA (FL2) by the measured sizes of red blood cells and platelets (FS) or the measured amount of granules (SS);
    constructing a scattergram of DNA concentration and RNA concentration; and
    sorting the cells in the blood using the scattergram.

2. The particle-sorting method according to claim 1, further comprising the steps of:
    detecting scattered light and fluorescence generated by irradiating light on the cells in the blood as electric signals;
    making a RNA histogram of red blood cells on the basis of the detected electric signals; and
    detecting a right-side address of the half peak of the RNA while detecting a doubled address thereof to sort a cluster on the right side as reticulocytes.

3. The particle-sorting method according to claim 1, wherein in the step of sorting cells, cellularly derived particles and noncellularly derived particles are sorted using the scattergram.

4. The particle-sorting method according to claim 1, wherein
    a center wavelength of the light irradiated on the cells in the blood is 408 nm, 445 nm, 473 nm or 488 nm.

5. The particle-sorting method according to claim 1, wherein
    the step of staining cells in the blood with acridine orange includes setting a sample prepared by mixing a staining agent containing acridine orange and a buffer with a blood specimen to a predetermined temperature, followed by staining the sample for a predetermined time.

6. The particle-sorting method according to claim 1, wherein
    the cells to be sorted include red blood cells, platelets, red blood cell fragments, nucleated red blood cells, malaria parasites, and Howell-Jolly bodies.

7. The particle-sorting method according to claim 1, further comprising the step of:
    determining staining behavior by judging whether a sample is stained well or not by determining in the scattergram the distribution positions of acridine orange-stained platelets and reticulocytes as well as distance between both positions.

8. The particle-sorting method according to claim 7, wherein
    the step of sorting the cells comprises defining a threshold level on the scattergram and then sorting red blood cells, platelets in the blood, cellular derived particles and non-cellular derived particles.

9. The particle-sorting method according to claim 7, wherein
    the step of determining staining behavior by using platelets as a staining indicator carries out the determination based on an orange-fluorescence component and/or green fluorescence component.

* * * * *